United States Patent [19]

Ito et al.

[11] Plant 4,117

[45] Oct. 4, 1977

[54] **RUBBER PLANT (*FICUS ELASTICA*)**

[76] Inventors: Tokuyasu Ito, 56 Kamiari-cho, 6-chome; Hideo Ikuta, 13-5, Aza Funae, Oaza Fushimi Okugaishinden, both of Hekinan, Aichi, Japan

[21] Appl. No.: 713,998

[22] Filed: Aug. 12, 1976

[30] Foreign Application Priority Data

Aug. 19, 1975 Japan ..... 50-99796

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—Armstrong, Nikaido & Marmelstein

[57] ABSTRACT

A rubber plant exhibiting border-variegated foliage and **resembling the known *Ficus elastica* Roxb. var. *decora*** tricolor hort., but bearing leaves having very narrow and distinct light-yellow border variegation and having a larger coriaceous oblong-shaped blade. Buds and young leaves are reddish in color. Propagation of new plants is easily accomplished by stem-cutting.

5 Drawing Figures

This invention relates to a new and distinct variety of a rubber plant having border-variegated foliage, *Ficus elastica* **Roxb. var. *decora* tricolor hort., which variety** is characterized particularly by its leaf blade having a very narrow and distinct light-yellow border on the edge of the leaf and by reddish buds and reddish young leaves.

This new variety of rubber plant was discovered on July 10, 1971 as a bud mutation while we were cultivating approximately 5,000 plants of a known variety of **rubber plant, *Ficus elastica* Roxb. var. *decora* tricolor** hort., at a greenhouse of Mr. Tokuyasu Ito, one of the inventors, located at No. 56, 6-chome, Kamiari-cho, Hekinan-shi, Aichi-ken, Japan. This plant of the known variety was first imported from West Germany to Japan around 1960 and propagated by Mr. Daizo Oguri residing at Iwasuberi-cho, Handa-shi, Aichi-ken, Japan. Some of the propagated plants were transferred to Mr. Ito and propagated by us since the summer of 1962. Ever since the finding of this new variety in 1971, we have propagated said new variety by stem-cutting (single eye cutting). It has been confirmed that the characteristics of this new variety are very uniform and stable in respective specimens.

Figure 1:
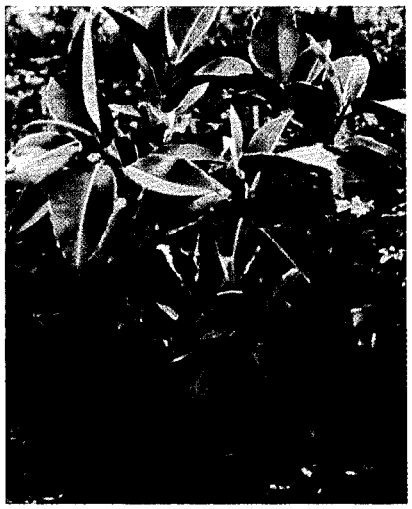
Figure 2A:
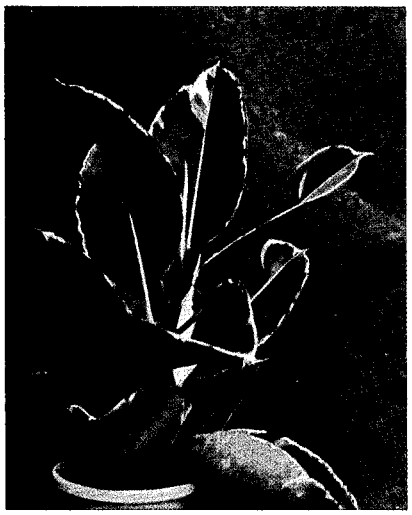
Figure 2B:
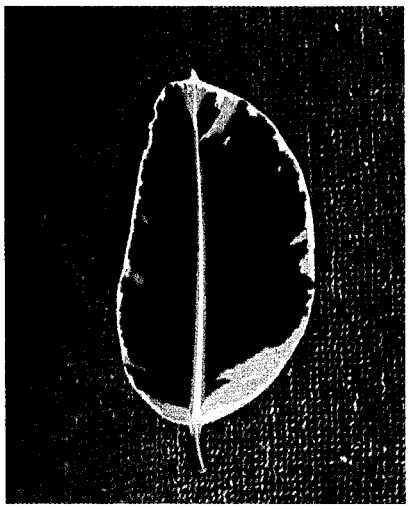
Figure 3A:
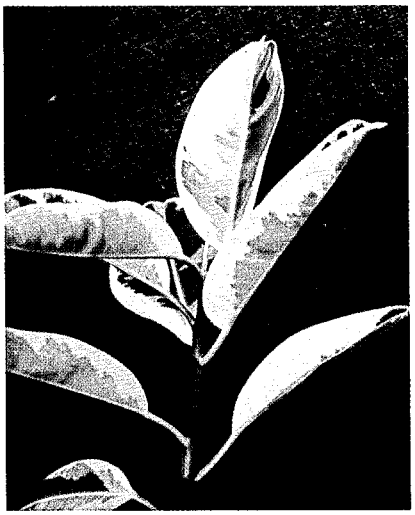
Figure 3B:
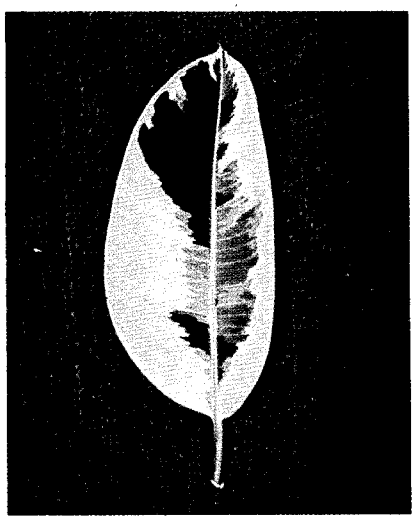

In the accompanying drawings,

FIG. 1 is a view of the 1971-discovered parent plant of the new variety of rubber plant, FIGS. 2A and 2B are views of a typical specimen of the new variety of rubber plant separated from the 1971-discovered parent and a plant, grown leaf of said specimen, respectively, and FIGS. 3A and 3B are views of a known variety of **rubber plant, *Ficus elastica* Roxb. var. *decora* tricolor** hort., and its grown leaf, respectively.

COMPARISON OF CHARACTERISTICS BETWEEN PARENT PLANT AND CULTIVATED SPECIMENS SEPARATED FROM THE PARENT PLANT BY STEM-CUTTING

Characteristics of the Parent Plant

The plant of the new variety is, as set forth hereinbefore, a bud mutation of the known variety, *Ficus elastica* **Roxb. var. *decora* tricolor hort. Since 1971, Scions have** been annually cut and propagated from the parent plant by the stem-cutting process, and, therefore, the growth characteristics of the parent plant are not as good as those of the specimens separated from the parent plant for cultivation. The resultant growth characteristics of the parent plant observed on Aug. 5, 1975 are as follows.

The plant is about 110 centimeters tall, and shoot growth in the rooted stem cuttings is very vigorous, said growing condition being substantially the same as that of the time when the bud mutation was first discovered in 1971.

Border variegation on the leaves is very stable and substantially uniform throughout all of the leaves, from the upper leaves to the lower leaves as shown in FIG. 1.

Grown leaves of the parent plant are about 28 centimeters in blade length, and 17 centimeters in blade width and about 4.5 centimeters in petiole length. These grown leaves are slightly smaller in size than those grown leaves of the specimens. The reason being that the process of stem-cutting has been carried out rather often.

Characteristics of the Specimens Exhibiting Border-variegated Foliage of the New Variety The entire plant shape of the new variety is substantially the same as that of the parent variety, *Ficus elastica* **Roxb. var. *decora* tricolor hort. However, the specimen** displays a less outwardly spreading tendency in its foliage (see in FIG. 2A), and the new variety exhibits fast and vigorous growth and enhanced resistance to cold weather conditions; thus, cultivation is easier.

The main difference between the new variety and the **known variety of *Ficus elastica* Roxb. var. *decora* tricolor hort., resides in the following. The leaf size of the new variety is somewhat larger than that of the known variety, and the leaf of the new variety is of an oblong shape with a thick coriaceous texture as seen in FIG. 2B.** The leaf blade is 34 to 35 centimeters long and 20 to 22 centimeters wide, and the petiole is 5 centimeters long. Buds and young leaves are reddish in color and enveloped with early defoliating stipules. Both upper and under surfaces of the leaf blade are smooth and lustrous.

A fully developed leaf is border-variegated. Although in a leaf of the known variety and light-yellow area is rather predominant and appears irregularly to form a so-called failed-border variegation (see FIG. 3B), in a leaf of the new variety, the proportion of the light-yellow area is relatively small and the light-yellow coloration distinctly appears on a relatively narrow area along the edge of the leaf to form a so-called thread like border variegation (see FIGS. 2A and 2B).

As set forth above, the plant of the new variety exhibits vigorous growth and good resistance to cold weather conditions. Defoliation of older leaves is much reduced as compared with the known variety. Grown leaves exhibiting the beautiful thread-like border variegation mentioned above do not fall off from the lower part of the tree for at least 4 or 5 years. Accordingly, the new variety is a foliage plant particularly suitable for potting.

Although propagation of the known rubber plants with variegated foliage, variety of *Ficus elastica* Roxb. **var. *decora* tricolor hort., including the parent plant of** the variety of the invention, by using cuttings is difficult or impossible, the plant of the new variety can be easily propagated by stem-cutting. Under an optimum rooting temperature condition of about 25° C, a bud and root will develop in about 25 days to such an extent that the young plants are capable of being transplanted.

What we claim is:

1. A new and distinct variety of *Ficus elastica* Roxb. **var. *decora* tricolor hort., substantially as herein shown** and described, characterized over the known rubber plant having variegated foliage, *Ficus elastica* Roxb. **var. *decora* tricolor hort., in that proportions of light-**yellow areas of the variegated leaves are small as a whole, said light-yellow areas appearing relatively narrow in size and are distinctly located on the edges of the leaves to form a so-called "thread-like border variegation"; leaves before development, namely buds and young leaves are reddish in color; grown leaves are larger in size than leaves of the known *Ficus elastica* **Roxb. var. *decora* tricolor hort. and have an oblong** shape with a thick coriaceous texture; and the new variety can be easily propagated by stem-cutting.

* * * * *

UNITED STATES PATENT OFFICE

CERTIFICATE OF CORRECTION

Patent No. P.P. 4,117 Dated October 4, 1977

Inventor(s) Tokuyasu Ito et al.

It is certified that error appears in the above-identified patent and that said Letters Patent are hereby corrected as shown below:

Delete the incorrect drawing figures and replace with the drawing figures as shown per attachments.

Signed and Sealed this

*Thirty-first* Day of *January 1978*

[SEAL]

*Attest:*

RUTH C. MASON
*Attesting Officer*

LUTRELLE F. PARKER
*Acting Commissioner of Patents and Trademarks*